(12) United States Patent
Josso et al.

(10) Patent No.: US 8,778,313 B2
(45) Date of Patent: Jul. 15, 2014

(54) AQUEOUS FLUID PHOTOPROTECTIVE COMPOSITIONS COMPRISING ESTER-TERMINATED POLY(ESTER AMIDE) POLYMERS

(75) Inventors: Martin Josso, Paris (FR); Cyril Chevalier, Juvisy-sur-Orge (FR); Anne-Laure Gaudry, Paris (FR)

(73) Assignee: L'Oreal, Paris (FR)

( * ) Notice: Subject to any disclaimer, the term of this patent is extended or adjusted under 35 U.S.C. 154(b) by 1694 days.

(21) Appl. No.: 11/653,868

(22) Filed: Jan. 17, 2007

(65) Prior Publication Data

US 2008/0115846 A1    May 22, 2008

Related U.S. Application Data

(60) Provisional application No. 60/762,127, filed on Jan. 26, 2006.

(30) Foreign Application Priority Data

Jan. 19, 2006    (FR) ...................................... 06 50192

(51) Int. Cl.
 *A61Q 17/04* (2006.01)
 *A61K 8/85* (2006.01)
 *A61K 8/88* (2006.01)

(52) U.S. Cl.
 CPC . *A61Q 17/04* (2013.01); *A61K 8/88* (2013.01); *A61K 8/85* (2013.01)
 USPC .......................................................... 424/59

(58) Field of Classification Search
 USPC .......................................................... 424/59
 See application file for complete search history.

(56) References Cited

U.S. PATENT DOCUMENTS

| | | | | |
|---|---|---|---|---|
| 6,126,948 A | * | 10/2000 | Simonnet et al. | ............. 424/401 |
| 6,139,827 A | | 10/2000 | Cohen et al. | |
| 2004/0151673 A1 | | 8/2004 | Josso | |
| 2004/0247549 A1 | | 12/2004 | Lu et al. | |
| 2004/0258644 A1 | * | 12/2004 | Simonnet | .................... 424/70.9 |
| 2005/0197479 A1 | | 9/2005 | Pavlin | |

FOREIGN PATENT DOCUMENTS

| | | | | |
|---|---|---|---|---|
| EP | 0979644 | * | 2/2000 | ............... A61K 7/32 |
| EP | 1 421 931 A2 | | 5/2004 | |
| WO | WO 02/092663 A1 | | 11/2002 | |
| WO | WO 2006/001940 A1 | | 1/2006 | |

OTHER PUBLICATIONS

Eastman products brochure CB-1T, Eastman Chemical Company, p. 10 (2009).*
European Search Report corresponding to EP 06 12 6913 issued on May 25, 2007, 6 pages.

* cited by examiner

*Primary Examiner* — Daniel Sullivan
*Assistant Examiner* — Barbara Frazier
(74) *Attorney, Agent, or Firm* — Buchanan Ingersoll & Rooney PC

(57) ABSTRACT

Enhanced SPF and/or reduced fluffing fluid compositions for photoprotecting the skin and/or the hair against the damaging effects of ultraviolet radiation, contain:
 (a) at least one photoprotective system capable of screening out UV radiation; and
 (b) at least one ester-terminated poly(ester amide) (ET-PEA) polymer, formulated into (c) a topically applicable, cosmetically acceptable aqueous support therefor; the subject aqueous compositions are advantageously vaporizable, especially in the form of sprays, confined within a pressurization device.

16 Claims, No Drawings

AQUEOUS FLUID PHOTOPROTECTIVE COMPOSITIONS COMPRISING ESTER-TERMINATED POLY(ESTER AMIDE) POLYMERS

CROSS-REFERENCE TO PRIORITY/PROVISIONAL APPLICATIONS

This application claims priority under 35 U.S.C. §119 of FR 06/50192, filed Jan. 19, 2006, and of U.S. Provisional Application No. 60/762,127, filed Jan. 26, 2006, each hereby expressly incorporated by reference and each assigned to the assignee hereof.

BACKGROUND OF THE INVENTION

1. Technical Field of the Invention

The present invention relates to fluid compositions for photoprotecting the skin and/or the hair against the damaging effects of ultraviolet radiation, comprising, formulated into a cosmetically acceptable aqueous support:

(a) at least one photoprotective system capable of screening out UV radiation; and (b) at least one ester-terminated poly(ester amide) (ET-PEA) polymer.

The present invention more particularly relates to aqueous vaporizable fluid compositions especially in the form of sprays, comprising a combination of:

(a) at least one photoprotective system capable of screening out UV radiation; and (b) at least one ester-terminated poly(ester amide) (ET-PEA) polymer.

This invention also relates to a device comprising (A) at least one reservoir containing at least one vaporizable fluid aqueous composition as defined above and (B) means for placing the said composition under pressure, in particular, of the non-aerosol pump type (atomizer) or of the aerosol or aerosol pump type.

2. Description of Background and/or Related and/or Prior Art

It is known that light radiation with wavelengths of from 280 nm to 400 nm permit tanning of the human epidermis and that rays with wavelengths of from 280 to 320 nm, which are known as UV-B rays, cause skin burns and erythema that can harm the development of a natural tan; this UV-B radiation should thus be screened out.

It is also known that UV-A rays, with wavelengths of from 320 to 400 nm, which cause tanning of the skin, are liable to induce impairment therein, especially in the case of sensitive skin or of skin that is continually exposed to solar radiation. UV-A rays, in particular, cause a loss of skin elasticity and the appearance of wrinkles, leading to premature aging. These promote the onset of the erythemal reaction or amplify this reaction in the case of certain individuals, and may even be the cause of phototoxic or photoallergic reactions. It is thus desirable also to screen out UV-A radiation.

Many photoprotective (UV-A and/or UV-B) cosmetic compositions for the skin have been proposed to date. Fluid formulations that afford for the users easy application to skin are most particularly desirable.

These anti-sun/sunscreen fluid compositions are quite often in the form of an emulsion of oil-in-water type (i.e., a cosmetically acceptable support consisting of an aqueous dispersing continuous phase and of an oily dispersed discontinuous phase) that contains, in varying concentrations, one or more standard lipophilic and/or hydrophilic organic screening agents capable of selectively absorbing the harmful UV radiation, these screening agents (and the amounts thereof) being selected as a function of the desired sun protection factor, the sun protection factor (SPF) being expressed mathematically as the ratio of the dose of UV radiation required to reach the erythema-forming threshold with the UV-screening agent, to the dose of UV radiation required to reach the erythema-forming threshold without UV-screening agent.

Thus, there is an increasing need for fluid anti-sun/sunscreen products with a high protection factor. These high protection factors may be reached by incorporating more screening agents in high concentrations. This is not always achievable, despite the addition of large amounts of screening agents. Furthermore, such amounts may result in impairment of the comfort (tacky, coarse effect and/or greasy effect).

Anti-sun/sunscreen products in spray form are increasingly sought by consumers, on account of their ease of use and their cosmetic pleasantness.

To satisfy this objective, it has already been recommended, in EP-1,421,931, to use spherical microparticles of porous silica. However, the sprays thus obtained have a tendency in certain cases to produce fluffing on the skin after application.

U.S. Patent Published Application No. 2003/0236387 discloses cosmetic compositions, especially makeup formulations in gel or solid composition form comprising at least one ester-terminated poly(ester amide) (ETPEA) polymer, in which the said polymer is present as gelling or structuring agent.

WO 2006/001940 discloses anti-sun/sunscreen emulsions comprising, as ester-terminated poly(ester amide) (ETPEA) polymer, the particular ester-terminated poly(ester amide) polymer bis-stearyl ethylenediamine/neopentyl glycol/stearyl hydrogenated dimer dilinoleate copolymer (INCI name) in which the said polymer is employed as an agent for improving the remanence to water and for reducing the migration of the product through the user's skin, and for limiting the slip-adhesion performance.

SUMMARY OF THE INVENTION

After considerable research conducted in the field of photoprotection indicated above, it has now been determined, surprisingly, that formulating an ester-terminated poly(ester amide) (ETPEA) polymer, into a fluid aqueous composition containing at least one system for screening out UV radiation, provides fluid anti-sun/sunscreen compositions with protection factors higher than those that may be obtained with the same photoprotective system alone, and, in particular, high-factor sprays, without the drawbacks and disadvantages mentioned above.

This discovery forms the basis of the present invention.

Thus, the present invention features novel fluid compositions for protecting the skin and/or the hair against ultraviolet radiation, comprising, formulated into a cosmetically acceptable aqueous support:

(a) at least one photoprotective system capable of screening out UV radiation; and (b) at least one ester-terminated poly(ester amide) (ET-PEA) polymer.

According to the invention, the term "photoprotective system capable of screening out UV radiation" generally means any compound or any combination of compounds which, via mechanisms known per se of absorption and/or reflection and/or scattering of UV-A and/or UV-B radiation, makes it possible to prevent, or at least to limit, the contact of the said radiation with a surface (skin or hair) onto which this or these compound(s) have been applied. In other words, these compounds may be UV-absorbing photoprotective organic screening agents or UV-scattering and/or UV-reflecting mineral (nano)pigments, and also mixtures thereof.

The term "cosmetically acceptable" means compatible with the skin and/or its integuments, which has a pleasant color, odor and feel and which does not cause any unacceptable discomfort (stinging, tautness or redness) liable to dissuade the consumer from using this composition.

The term "fluid composition" means a composition that is not in a solid form. Its viscosity may be measured using a Rheomat 180 viscometer at 25° C. at a spin speed of 200 rpm after spinning for 30 seconds, and is preferably less than 2 Pa·s.

The present invention also features formulating at least one ester-terminated poly(ester amide) (ETPEA) polymer into a fluid composition comprising, in a cosmetically acceptable aqueous support, at least one photoprotective system capable of screening out UV radiation, for the purpose of increasing the sun protection factor (SPF) thereof.

This invention also features formulating at least one ester-terminated poly(ester amide) (ETPEA) polymer into a fluid composition comprising, in a cosmetically acceptable aqueous support, at least one photoprotective system capable of screening out UV radiation, for the purpose of reducing or even eliminating the fluffing effect thereof.

Other characteristics, aspects and advantages of the present invention will emerge from the detailed description that follows.

DETAILED DESCRIPTION OF BEST MODE AND SPECIFIC/PREFERRED EMBODIMENTS OF THE INVENTION

The ester-terminated poly(ester amide) (ETPEA) polymers in accordance with the invention are preferably in the form of a resin prepared by reacting a diacid, a diamine, a polyol and a monoalcohol, in which:

(i) at least 50 equivalent % of the said diacid comprises a polymerized fatty acid and (ii) at least 50 equivalent % of the said diamine comprises ethylenediamine.

More preferentially, the resin composition is such that:

(iii) 10 to 60 equivalent % relative to the total of the equivalents of hydroxyl and of amine originating from the diamine, from the polyol and from the monoalcohol are derived from the monoalcohol.

(iv) not more than 50 equivalent % relative to the total of the equivalents of hydroxyl and of amine originating from the diamine, from the polyol and from the monoalcohol are derived from the polyol.

The ester-terminated poly(ester amide) (ETPEA) polymers in accordance with the invention may be prepared according to the process described in U.S. Pat. No. 6,552,160.

The diacid is generally an organic molecule containing two carboxylic acid groups or equivalent reactive groups. The diacid is preferentially a polymerized fatty acid.

The polymerized fatty acid is typically a mixture comprising an acid dimer and an acid trimer, in which each dimer may be saturated, unsaturated, cyclic, acyclic, etc. The polymerized fatty acid used for the synthesis of the ester-terminated poly(ester amide) (ETPEA) polymer is preferably an acid dimer.

The polymerized fatty acid is generally formed by heating long-chain unsaturated fatty acids, for example $C_{18}$ carboxylic monoacids, to temperatures of about 200°-250° C. in the presence of a catalytic clay to polymerize the fatty acids. The product obtained generally comprises an acid dimer, in particular, a $C_{36}$ dicarboxylic acid formed by dimerization of the fatty acid and an acid trimer, in particular, a $C_{54}$ tricarboxylic acid obtained by trimerization of the carboxylic acid. Further details regarding the polymerization of fatty acids are given, in particular, in U.S. Pat. No. 3,157,681 and in the publication "Naval Stores—Production, Chemistry and Utilization, D. F. Zinkel and J. Russell (eds), *Pulp. Chem. Assoc. Inc.*, 1989, chapter 23".

Preferentially, the polymerized fatty acid contains less than 20% by weight of acid trimer and at least 80% by weight of acid dimer relative to the total weight of the polymerized fatty acid. More particularly, the acid dimer constitutes essentially all of the polymerized fatty acid.

Among the unsaturated fatty acids used to form the polymerized fatty acid, exemplary are oleic acid, linoleic acid and linolenic acid. Long-chain fatty acid oils are preferably used, which are mixtures of long-chain unsaturated acids obtained via a process of reducing wood to pulp. Other sources may also be used, for instance soybean seeds or canola. The polymerized fatty acid according to the invention advantageously has an acid number of about from 180 to 200.

The polymerized fatty acid may be hydrogenated before being used in the resin-forming reaction. The hydrogenation makes it possible to obtain a slightly higher resin melting point and also greater stability to oxidation and color stability in the case of a slightly colored resin.

Among the polymerized fatty acids and especially the hydrogenated forms that are commercially available, exemplary are the product marketed under the trademark Unidyme by Arizona Chemical, the product marketed under the trademark Pripol 1015 by Uniqema, or the product marketed under the trademark Empol 1008 by Cognis.

A $C_{36}$ hydrogenated linoleic acid dimer will more particularly be used as polymerized fatty acid.

In addition to the polymerized fatty acid or reactive equivalents, the diacid may comprise a co-diacid of formula HOOC—$R_1$—COOH in which $R_1$ is a $C_4$-$C_{19}$, preferably $C_4$-$C_{12}$ and more preferentially $C_4$-$C_8$ hydrocarbon-based compound.

The carbon atoms may be arranged in linear, branched or cyclic form and an unsaturation may be present from two adjacent atoms. $R_1$ may be aliphatic or aromatic.

The diamine reagent contains two amine groups, which are preferably primary amines and represented by the formula: $HN(R_{2a})$—$R_2$—$N(R_{2a})H$ in which $R_{2a}$ denotes hydrogen or an alkyl group or forms a heterocycle with $R_2$ or another radical $R_{2a}$.

Ethylenediamine, i.e., $R_{2a}$ is hydrogen and $R_2$ is —$CH_2$—$CH_2$—, will be used more particularly as diamine.

The diamines other than ethylenediamine will be referred to herein as co-diamines. When they are present, the co-diamines are used in small amounts relative to the ethylenediamine.

The monoalcohol may be represented by the formula $R_3$—OH in which $R_3$ is preferably a hydrocarbon-based group containing at least 10 carbon atoms. Thus, the monoalcohol may be described as a monohydric alcohol.

According to one particular embodiment, $R_3$ is a $C_{10}$-$C_{30}$ hydrocarbon-based group, preferentially a $C_{12}$-$C_{24}$ hydrocarbon-based group and even more particularly a $C_{18}$ hydrocarbon-based radical. For the purposes of the invention, the term "$C_{10}$-$C_{30}$ hydrocarbon-based group" means any group containing at least 10 carbon atoms but not more than 30 carbon atoms. The carbon atoms may be arranged in a linear, branched or cyclic manner and the hydrocarbon-based radical may be saturated or unsaturated.

According to one particularly preferred embodiment, $R_3$ is linear and the hydroxyl group is located on a terminal carbon:

i.e., the monoalcohol is primary. Among the monoalcohols that may be used to prepare the ETPEA resin, exemplary are 1-dodecanol, 1-tetradecanol, 1-hexadecanol (cetyl alcohol), 1-octadecanol (stearyl alcohol), 1-eicosanol (arachidyl alcohol) and 1-docosanol (behenyl alcohol).

The reactive monoalcohol may contain an alkylene group, i.e., an alkyl group containing an unsaturation from two adjacent carbon atoms.

Another reactive monoalcohol that may be used according to the invention may be a Guerbet alcohol of formula H—C($R_a$)($R_b$)—$CH_2$—OH in which $R_a$ and $R_b$, which may be identical or different, preferably denote a $C_6$-$C_{12}$ hydrocarbon-based group. Guerbet alcohols are especially described in the publication. "Dictionary For Auxiliaries For Pharmacy, Cosmetics And Related Fields", H.P. Fiedler, 3rd edition, 1989, Cantor Aulendorf. Hexadecyl-2-octadecanol containing 24 carbon atoms will be used more particularly.

Another type of reactive monoalcohol that may be used according to the invention is a linear alcoholic wax. Among the commercially available linear alcoholic waxes that are exemplary are the products marketed under the trademark Unilin by Petrolite Corporation (Tulsa, Okla.). These linear alcoholic waxes are generally a mixture of linear alcohols containing at least 20 carbon atoms and more particularly at least 24 carbon atoms.

The technique of Vapor-Pressure Osmometry (VPO) may be used to characterize the number-average molecular weight of a mixture of alcohols. According to one particular embodiment, the mixture of monoalcoholic linear waxes has a number-average molecular weight measured by VPO from about 200 to about 800 and preferably from about 300 to about 600. A pure $C_{22}$ linear monohydric alcohol has a molecular weight measured by VPO of 326.

In accordance with the present invention, a pure linear monoalcohol or mixture of monoalcohols will be used, for instance: 1-eicosanol ($C_{20}$), 1-docosanol ($C_{22}$, behenyl alcohol), dotriacontanol ($C_{32}$), tetratriacontanol ($C_{34}$), pentatriacontanol ($C_{35}$), tetracontanol ($C_{40}$), tetraacontanol ($C_{44}$), dopentaacontanol ($C_{54}$), tetrahexaacontanol ($C_{64}$), dohexaacontanol ($C_{72}$).

1-Octadecanol, more commonly known as stearyl alcohol, will be used more particularly.

A final ingredient necessary for preparing the ETPEA resin is a polyol or polyhydric alcohol. The polyol has the structure: $R_4(OH)_n$ in which $R_4$ denotes an n-valent organic group. For example, $R_4$ may be a $C_2$-$C_{20}$ organic group without hydroxyl substitution. As another example, $R_4$ may be a hydrocarbon-based group. n is generally equal to 2, 3, 4, 5 or 6.

Among the polyols that may be used according to the invention, exemplary are ethylene glycol, propylene glycol, butylene glycol, glycerol, trimethylolpropane, pentaerythritol, neopentyl glycol, tris(hydroxymethyl)methanol, dipentaerythritol and tripentaerythritol.

Neopentyl glycol will more particularly be used.

Diacid-equivalent reagents and/or diamine-equivalent reagents may also be used for the preparation of the ETPEA resin. For example, diesters may be used in place of some or all of the diacids in the reaction forming the ETPEA resin. The term "diester" means any product of esterification of a diacid with molecules containing a hydroxyl function. Such diesters are preferably obtained from relatively volatile molecules containing hydroxyl functions in order for the said molecules to be able to be removed easily from the reaction vessel after the reaction of the monoalcohol and/or of the diamine with the diester. A lower diester, in particular, a product of esterification or diesterification of a diacid as defined above with a $C_1$-$C_4$ monoalcohol (i.e., methanol, ethanol, propanol and butanol), may be used in place of some or all of the diacids in the reaction forming the ETPEA resin. Acid halides may also be used in place of some or all of the diacids in the reaction forming the ETPEA resin. Similarly, the monoalcohol may be esterified with a volatile diacid, for example: acetic acid, before being used in the reaction forming the ETPEA resin. Such equivalent reagents are, however, only preferential insofar as they introduce reactive groups into the reaction vessel.

Preferentially, the carboxylic acid equivalents should be substantially equal to the combined hydroxyl equivalents provided by the monoalcohol and the polyol and amine equivalents provided by the diamine. In other words, each of the acid and amine numbers of the resin in accordance with the invention should preferably be less than 25, more preferentially less than 15 and more particularly less than 10, more particularly less than 5.

When a co-diacid is used to prepare the ETPEA resin, the co-diacid should not represent more than 50% of the carboxylic acid equivalents in the reaction mixture. In other words, the co-diacid is from 0 to 50 equivalent %, more preferentially from 0 to 25% and even more preferentially from 0 to 10% of the acid equivalents in the reaction mixture.

When a co-diamine is used to prepare the ETPEA resin, the co-diacid should not represent more than 50% of the carboxylic acid equivalents in the reaction mixture. In other words, the co-diamine is from 0 to 50 equivalent %, more preferentially from 0 to 25% and even more preferentially from 0 to 10% of the acid equivalents in the reaction mixture.

The hydroxyl equivalents originating from the polyol are preferably less than or equal to 50% relative to the total amount of hydroxyl and amine equivalents provided by the polyol, monoalcohol and diamine reagents. According to one particular embodiment of the invention, the hydroxyl equivalents originating from the polyol may be less than or equal to 40%, or less than or equal to 30% or even less than or equal to 20% relative to the total amount of hydroxyl and amine equivalents provided by the polyol, monoalcohol and diamine reagents.

The amine equivalents preferably range from 0.3 to 0.75 relative to the total amount of hydroxyl and amine equivalents provided by the polyol, monoalcohol and diamine reagents. According to one particular embodiment of the invention, the hydroxyl equivalents originating from the polyol range from 0.05 to 0.45 relative to the total amount of hydroxyl and amine equivalents provided by the polyol, monoalcohol and diamine reagents. According to one particular embodiment of the invention, the hydroxyl equivalents originating from the monoalcohol range from 0.20 to 0.45 relative to the total amount of hydroxyl and amine equivalents provided by the polyol, monoalcohol and diamine reagents.

The ester-terminated poly(esteramide) polymer bis-stearyl ethylenediamine/neopentyl glycol/stearyl hydrogenated dimer dilinoleate copolymer (INCI name), which is a copolymer of hydrogenated linoleic diacid, of ethylenediamine, of neopentyl glycol and of stearyl alcohol, will be used more particularly. This copolymer is especially marketed under the trademark Sylvaclear C75 V by Arizona Chemical.

The ester-terminated poly(ester amide) polymer in accordance with the invention is present in the composition preferably in a maximum amount of 10% by weight, more preferentially from 0.1% to 10% by weight, even more preferentially from 0.5% to 5% and even more particularly from 1% to 3% relative to the total weight of the composition.

According to the invention, the photoprotective system may contain one or more hydrophilic, lipophilic or insoluble organic screening agents and/or one or more mineral (nano)

pigments. Preferentially, it will contain at least one hydrophilic, lipophilic or insoluble organic UV-screening agent.

The hydrophilic, lipophilic or insoluble organic UV-screening agents are selected especially from among anthranilates; dibenzoylmethane derivatives; cinnamic derivatives; salicylic derivatives; camphor derivatives; benzophenone derivatives; β,β-diphenylacrylate derivatives; triazine derivatives; benzotriazole derivatives; benzalmalonate derivatives, especially those cited in U.S. Pat. No. 5,624,663; benzimidazole derivatives; imidazolines; bis-benzazolyl derivatives as described in EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2,303, 549, DE-197,26,184 and EP-893,119; benzoxazole derivatives as described in EP-0,832,642, EP-1,027,883, EP-1,300, 137 and DE-101,62,844; screening polymers and screening silicones such as those described especially in WO 93/04665; α-alkylstyrene-based dimers, such as those described in DE-98,5,49; 4,4-diarylbutadienes such as those described in EP-0,967,200, DE-197,46,654, DE-197,55,649, EP-A-1, 008,586, EP-1,133,980 and EP-133,981, and mixtures thereof.

As examples of organic photoprotective agents, representative are those denoted hereinbelow under their INCI name:

para-Aminobenzoic Acid Derivatives:
PABA,
Ethyl PABA,
Ethyl dihydroxypropyl PABA,
Ethylhexyl dimethyl PABA marketed, in particular, under the trademark "Escalol 507" by ISP,
Glyceryl PABA,
PEG-25 PABA marketed under the trademark "Uvinul P25" by BASF.
  Dibenzoylmethane Derivatives:
Butylmethoxydibenzoylmethane marketed especially under the trademark "Parsol 1789" by Hoffmann LaRoche,
Isopropyldibenzoylmethane.
  Salicylic Derivatives:
Homosalate marketed under the trademark "Eusolex HMS" by Rona/EM Industries,
Ethylhexyl salicylate marketed under the trademark "Neo Heliopan OS" by Haarmann and Reimer,
Dipropylene glycol salicylate marketed under the trademark "Dipsal" by Scher,
TEA salicylate marketed under the trademark "Neo Heliopan TS" by Haarmann and Reimer.
  Cinnamic Derivatives:
Ethylhexyl methoxycinnamate marketed, in particular, under the trademark "Parsol MCX" by Hoffmann LaRoche,
Isopropyl methoxycinnamate,
Isoamyl methoxycinnamate marketed under the trademark "Neo Heliopan E 1000" by Haarmann and Reimer,
Cinoxate,
DEA methoxycinnamate,
Diisopropyl methylcinnamate,
Glyceryl ethylhexanoate dimethoxycinnamate.
  β,β-Diphenylacrylate Derivatives:
Octocrylene marketed, in particular, under the trademark "Uvinul N539" by BASF,
Etocrylene marketed, in particular, under the trademark "Uvinul N35" by BASF.
  Benzophenone Derivatives:
Benzophenone-1 marketed under the trademark "Uvinul 400" by BASF,
Benzophenone-2 marketed under the trademark "Uvinul D50" by BASF,
Benzophenone-3 or Oxybenzone marketed under the trademark "Uvinul M40" by BASF,
Benzophenone-4 marketed under the trademark "Uvinul MS40" by BASF, Benzophenone-5,
Benzophenone-6 marketed under the trademark "Helisorb 11" by Norquay,
Benzophenone-8 marketed under the trademark "SpectraSorb UV-24" by American Cyanamid,
Benzophenone-9 marketed under the trademark "Uvinul DS49" by BASF, Benzophenone-12
n-hexyl 2-(4-diethylamino-2-hydroxybenzoyl)benzoate.
  Benzylidenecamphor Derivatives:
3-Benzylidenecamphor manufactured under the trademark "Mexoryl SD" by Chimex,
4-Methylbenzylidenecamphor marketed under the trademark "Eusolex 6300" by Merck,
Benzylidenecamphorsulfonic acid manufactured under the trademark "Mexoryl SL" by Chimex,
Camphor benzalkonium methosulfate manufactured under the trademark "Mexoryl SO" by Chimex,
Terephthalylidenedicamphorsulfonic acid manufactured under the trademark "Mexoryl SX" by Chimex,
Polyacrylamidomethylbenzylidenecamphor manufactured under the trademark "Mexoryl SW" by Chimex.
  Phenylbenzimidazole Derivatives:
Phenylbenzimidazolesulfonic acid marketed, in particular, under the trademark "Eusolex 232" by Merck,
Disodium phenyl dibenzimidazole tetrasulfonate marketed under the trademark "Neo Heliopan AP" by Haarmann and Reimer.
  Phenylbenzotriazole Derivatives:
Drometrizole trisiloxane marketed under the trademark "Silatrizole" by Rhodia Chimie,
Methylenebis(benzotriazolyl)tetramethylbutylphenol marketed in solid form under the trademark "MIXXIM BB/100" by Fairmount Chemical, or in micronized form as an aqueous dispersion under the trademark "Tinosorb M" by Ciba Specialty Chemicals.
  Triazine Derivatives:
bis-Ethylhexyloxyphenol Methoxyphenyl Triazine marketed under the trademark "Tinosorb S" by Ciba Geigy, Ethylhexyltriazone marketed, in particular, under the trademark "Uvinul T150" by BASF,
Diethylhexylbutamidotriazone marketed under the trademark "Uvasorb HEB" by Sigma 3V,
2,4,6-tris(dineopentyl 4'-aminobenzalmalonate)-s-triazine,
2,4,6-tris(diisobutyl 4'-aminobenzalmalonate)-s-triazine.
  Anthranilic Derivatives:
Menthyl anthranilate marketed under the trademark "Neo Heliopan MA" by Haarmann and Reimer.
  Imidazoline Derivatives:
Ethylhexyldimethoxybenzylidenedioxoimidazoline propionate.
  Benzalmalonate Derivatives:
Dineopentyl 4'-methoxybenzalmalonate,
Polyorganosiloxane containing benzalmalonate functions, for instance Polysilicone-15, marketed under the trademark "Parsol SLX" by Hoffmann LaRoche.
  4,4-Diarylbutadiene Derivatives:
1,1-Dicarboxy(2,2'-dimethylpropyl)-4,4-diphenylbutadiene.
  Benzoxazole Derivatives:
2,4-bis[5-(1-dimethylpropyl)benzoxazol-2-yl(4-phenyl)imino]-6-(2-ethylhexyl)imino-1,3,5-triazine marketed under the trademark Uvasorb K2A by Sigma 3V
and mixtures thereof.

The preferred organic agents for screening out UV radiation are selected from among:

Ethylhexyl Methoxycinnamate,
Homosalate,
Ethylhexyl salicylate,
Butylmethoxydibenzoylmethane,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Ethylhexyl Triazone,
bis-Ethylhexyloxyphenol Methoxyphenyl Triazine,
Diethylhexyl Butamido Triazone,
2,4,6-tris(Dineopentyl 4'-aminobenzalmalonate)-s-triazine,
2,4,6-tris(Diisobutyl 4'-aminobenzalmalonate)-s-triazine,
Methylenebis(benzotriazolyl)tetramethylbutylphenol,
Drometrizole trisiloxane,
Polysilicone-15,
Dineopentyl 4'-methoxybenzalmalonate,
1,1-Dicarboxy(2,2'-dimethylpropyl)-4,4-diphenylbutadiene,
2,4-Bis[5-1 (dimethylpropyl)benzoxazol-2-yl(4-phenyl)imino]-6-(2-ethylhexyl)imino-1,3,5-triazine,
and mixtures thereof.

The inorganic screening agents are selected from among pigments or nanopigments (mean size of the primary particles: generally from 5 nm to 100 nm and preferably from 10 nm to 50 nm) of coated or uncoated metal oxides, for instance nanopigments of titanium oxide (amorphous or crystallized in rutile and/or anatase form), of iron oxide, of zinc oxide, of zirconium oxide or of cerium oxide, which are all UV photoprotective agents that are well known per se.

The pigments may be coated or uncoated.

The coated pigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithin is, sodium, potassium, zinc, iron or aluminum salts of fatty acids, metal alkoxides (of titanium or of aluminum), polyethylene, silicones, proteins (collagen, elastin), alkanolamines, silicon oxides, metal oxides or sodium hexametaphosphate.

As is known, silicones are organosilicon polymers or oligomers of linear or cyclic, branched or crosslinked structure, of variable molecular weight, obtained by polymerization and/or polycondensation of suitably functionalized silanes, and consist essentially of a repetition of main units in which the silicon atoms are linked together via oxygen atoms (siloxane bond), optionally substituted hydrocarbon-based radicals being directly attached via a carbon atom to the said silicon atoms.

The term "silicones" also includes the silanes required for their preparation, in particular, alkyl silanes.

The silicones used for coating the nanopigments that are suitable for the present invention are preferably selected from the group consisting of alkyl silanes, polydialkylsiloxanes and polyalkylhydrogenosiloxanes. Even more preferentially, the silicones are selected from the group consisting of octyltrimethylsilane, polydimethylsiloxanes and polymethylhydrogenosiloxanes.

Needless to say, before being treated with silicones, the metal oxide pigments may have been treated with other surface agents, in particular, with cerium oxide, alumina, silica, aluminum compounds or silicon compounds, or mixtures thereof.

The coated pigments are more particularly titanium oxides that have been coated:
with silica, such as the product "Sunveil" from Ikeda and the product "Eusolex T-AVO" from Merck,
with silica and iron oxide, such as the product "Sunveil F" from Ikeda,
with silica and alumina, such as the products "Microtitanium Dioxide MT 500 SA" and "Microtitanium Dioxide MT 100 SA" from Tayca, "Tioveil" from Tioxide and "Mirasun TiW 60" from Rhodia,
with alumina, such as the products "Tipaque TTO-55 (B)" and "Tipaque TTO-55 (A)" from Ishihara and "UVT 14/4" from Kemira,
with alumina and aluminum stearate, such as the product "Microtitanium Dioxide MT 100 TV, MT 100 TX, MT 100 Z and MT-01 from Tayca, and the products "Solaveil CT-10 W", "Solaveil CT 100" and "Solaveil CT 200" from Uniqema,
with silica, alumina and alginic acid, such as the product "MT-100 AQ" from Tayca,
with alumina and aluminum laurate, such as the product "Microtitanium Dioxide MT 100 S" from Tayca,
with iron oxide and iron stearate, such as the product "Microtitanium Dioxide MT 100 F" from Tayca,
with zinc oxide and zinc stearate, such as the product "BR351" from Tayca,
with silica and alumina and treated with a silicone, such as the products "Microtitanium Dioxide MT 600 SAS", "Microtitanium Dioxide MT 500 SAS" or "Microtitanium Dioxide MT 100 SAS" from Tayca,
with silica, alumina and aluminum stearate and treated with a silicone, such as the product "STT-30-DS" from Titan Kogyo,
with silica and treated with a silicone, such as the product "UV-Titan X 195" from Kemira, or the product SMT-100 WRS from Tayca,
with alumina and treated with a silicone, such as the products "Tipaque TTO-55 (S)" from Ishihara or "UV Titan M 262" from Kemira,
with triethanolamine, such as the product "STT-65-S" from Titan Kogyo,
with stearic acid, such as the product "Tipaque TTO-55 (C)" from Ishihara,
with sodium hexametaphosphate, such as the product "Microtitanium Dioxide MT 150 W" from Tayca.

Other titanium oxide pigments treated with a silicone are preferably $TiO_2$ treated with octyltrimethylsilane and for which the mean size of the elementary particles is from 25 to 40 nm, such as the product marketed under the trademark "T 805" by Degussa Silices, $TiO_2$ treated with a polydimethylsiloxane and for which the mean size of the elementary particles is 21 nm, such as the product marketed under the trademark "70250 Cardre UF TiO2SI3" by Cardre, anatase/rutile $TiO_2$ treated with a polydimethylhydrogenosiloxane and for which the mean size of the elementary particles is 25 nm, such as the product marketed under the trademark "Microtitanium Dioxide USP Grade Hydrophobic" by Color Techniques.

The uncoated titanium oxide pigments are marketed, for example, by Tayca under the trademarks "Microtitanium Dioxide MT 500 B" or "Microtitanium Dioxide MT 600 B", by Degussa under the trademark "P 25", by Wacker under the trademark "Transparent titanium oxide PW", by Myoshi Kasei under the trademark "UFTR", by Tomen under the trademark "ITS" and by Tioxide under the trademark "Tioveil AQ".

The uncoated zinc oxide pigments are, for example:
those marketed under the trademark "Z-Cote" by Sunsmart;
those marketed under the trademark "Nanox" by Elementis;
those marketed under the trademark "Nanogard WCD 2025" by Nanophase Technologies.

The coated zinc oxide pigments are, for example:
those marketed under the trademark "Z-Cote HP1" by Sunsmart (dimethicone-coated ZnO);
those marketed under the trademark "Zinc Oxide CS-5" by Toshibi (ZnO coated with polymethylhydrogenosiloxane);
those marketed under the trademark "Nanogard Zinc Oxide FN" by Nanophase Technologies (as a 40% dispersion in Finsolv TN, $C_{12}$-$C_{15}$ alkyl benzoate);
those marketed under the trademark "Daitopersion ZN-30" and "Daitopersion ZN-50" by Daito (dispersions in cyclopolymethylsiloxane/oxyethylenated polydimethylsiloxane, containing 30% or 50% of nanozinc oxides coated with silica and polymethylhydrogenosiloxane);
those marketed under the trademark "NFD Ultrafine ZNO" by Daikin (ZnO coated with perfluoroalkyl phosphate and copolymer based on perfluoroalkylethyl as a dispersion in cyclopentasiloxane);
those marketed under the trademark "SPD-Z1" by Shin-Etsu (ZnO coated with silicone-grafted acrylic polymer, dispersed in cyclodimethylsiloxane);
those marketed under the trademark "Escalol Z100" by ISP (alumina-treated ZnO dispersed in an ethylhexyl methoxycinnamate/PVP-hexadecene/methicone copolymer mixture);
those marketed under the trademark "Fuji ZNO-SMS-10" by Fuji Pigment (ZnO coated with silica and polymethylsilsesquioxane);
those marketed under the trademark "Nanox Gel TN" by Elementis (ZnO dispersed at a concentration of 55% in $C_{12}$-$C_{15}$ alkyl benzoate with hydroxystearic acid polycondensate).

The uncoated cerium oxide pigments are marketed under the trademark "Colloidal Cerium Oxide" by Rhone-Poulenc.

The uncoated iron oxide nanopigments are marketed, for example, by Arnaud under the trademarks "Nanogard WCD 2002 (FE 45B)", "Nanogard Iron FE 45 BL AQ", "Nanogard FE 45R AQ" and "Nanogard WCD 2006 (FE 45R)" or by Mitsubishi under the trademark "TY-220", The coated iron oxide pigments are marketed, for example, by Arnaud under the trademarks "Nanogard WCD 2008 (FE 45B FN)", "Nanogard WCD 2009 (FE 45B 556)", "Nanogard FE 45 BL 345" and "Nanogard FE 45 BL" or by BASF under the trademark "Transparent Iron Oxide".

Also exemplary are mixtures of metal oxides, especially of titanium dioxide and of cerium dioxide, including the silica-coated equal-weight mixture of titanium dioxide and of cerium dioxide, marketed by Ikeda under the trademark "Sunveil A", and also the alumina, silica and silicone-coated mixture of titanium dioxide and of zinc dioxide, such as the product "M 261" marketed by Kemira, or the alumina, silica and glycerol-coated mixture of titanium dioxide and of zinc dioxide, such as the product "M 211" marketed by Kemira.

The photoprotective system according to the invention is preferably present in the subject compositions in a content ranging from 0.1% to 40% by weight and, in particular, from 5% to 25% by weight relative to the total weight of the composition.

The compositions according to the invention may also contain agents for artificially tanning and/or browning the skin (self-tanning agents) and more particularly dihydroxyacetone (DHA). They are preferably present in amounts ranging from 0.1% to 10% by weight relative to the total weight of the composition.

The aqueous compositions in accordance with the present invention may also comprise standard cosmetic adjuvants selected especially from among fatty substances, organic solvents, ionic or non-ionic, hydrophilic or lipophilic thickeners, softeners, humectants, opacifiers, stabilizers, emollients, silicones, anti-foams, fragrances, preservatives, anionic, cationic, non-ionic, zwitterionic or amphoteric surfactants, active agents, fillers, polymers, propellants, acidifying or basifying agents or any other ingredient usually used in cosmetics and/or dermatology.

The fatty substances may be an oil or a wax other than the apolar waxes as defined above, or mixtures thereof. The term "oil" means a compound that is liquid at room temperature. The term "wax" means a compound that is solid or substantially solid at room temperature and whose melting point is generally greater than 35° C.

Oils are exemplary include mineral oils (paraffin); plant oils (sweet almond oil, macadamia oil, grapeseed oil or jojoba oil); synthetic oils, for instance perhydrosqualene, fatty alcohols or fatty amides (for instance isopropyl lauroyl sarcosinate marketed under the trademark "Eldew SL-205" by Ajinomoto), fatty acids or fatty esters (for instance the $C_{12}$-$C_{15}$ alkyl benzoate marketed under the trademark "Finsolv TN" or "Witconol TN" by Witco, octyl palmitate, isopropyl lanolate and triglycerides, including capric/caprylic acid triglycerides, and dicaprylyl carbonate marketed under the trademark "Cetiol CC" by Cognis), oxyethylenated or oxypropylenated fatty esters and ethers; silicone oils (cyclomethicone and polydimethylsiloxanes, or PDMS) or fluoro oils, and polyalkylenes.

Waxy compounds that are exemplary include carnauba wax, beeswax, hydrogenated castor oil, polyethylene waxes and polymethylene waxes, for instance the product marketed under the trademark Cirebelle 303 by Sasol.

Among the organic solvents that are exemplary are lower alcohols and polyols. These polyols may be selected from glycols and glycol ethers, for instance ethylene glycol, propylene glycol, butylene glycol, dipropylene glycol or diethylene glycol.

Hydrophilic thickeners that are exemplary include carboxyvinyl polymers such as the Carbopol products (carbomers) and the Pemulen products (acrylate/C10-C30-alkylacrylate copolymer); polyacrylamides, for instance the crosslinked copolymers marketed under the trademarks Sepigel 305 (CTFA name: polyacrylamide/C13-14 isoparaffin/Laureth 7) or Simulgel 600 (CTFA name: acrylamide/sodium acryloyidimethyltaurate copolymer/isohexadecane/polysorbate 80) by SEPPIC; 2-acrylamido-2-methylpropanesulfonic acid polymers and copolymers, which are optionally crosslinked and/or neutralized, for instance the poly(2-acrylamido-2-methylpropanesulfonic acid) marketed by Hoechst under the trademark "Hostacerin AMPS" (CTFA name: ammonium polyacryloyldimethyltaurate) or Simulgel 800 marketed by SEPPIC (CTFA name: sodium polyacryloyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 marketed by SEPPIC; cellulose-based derivatives such as hydroxyethylcellulose; polysaccharides and especially gums such as xanthan gum; and mixtures thereof.

Lipophilic thickeners that are exemplary include synthetic polymers such as poly($C_{10}$-$C_{30}$ alkyl acrylates) marketed under the trademark "Intelimer IPA 13-1" and "Intelimer IPA 13-6" by Landec, or modified clays such as hectorite and its derivatives, for instance the products marketed under the trademark bentone.

Among the active agents that are exemplary are:
vitamins (A, C, E, K, PP, etc.) and derivatives or precursors thereof, alone or as mixtures;
anti-pollution agents and/or free-radical scavengers;
depigmenting agents and/or propigmenting agents;
anti-glycation agents;
calmatives;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
tensioning agents;
matting agents;
keratolytic agents;
desquamating agents;
moisturizers;
anti-inflammatory agents;
agents acting on the energy metabolism of cells;
insect repellants;
substance P or CGRP antagonists;
hair-loss counteractants and/or hair restorers;
anti-wrinkle agents.

Needless to say, one skilled in this art will take care to select the optional additional compound(s) mentioned above and/or the amounts thereof such that the advantageous properties intrinsically associated with the compositions in accordance with the invention are not, or are not substantially, adversely affected by the envisaged addition(s).

The compositions according to the invention may be formulated according to techniques that are well known to those skilled in this art. They may be, in particular, in the form of a simple or complex emulsion (O/W, W/O, O/W/O or W/O/W emulsion) such as a cream, a milk or a cream-gel; in the form of an aqueous gel; in the form of a lotion. They may optionally be packaged as an aerosol and may be in the form of a mousse or a spray.

The compositions according to the invention are preferably in the form of an oil-in-water or water-in-oil emulsion.

The emulsions generally contain at least one emulsifier selected from among amphoteric, anionic, cationic and non-ionic emulsifiers, which are used alone or as a mixture. The emulsifiers are appropriately selected according to the emulsion to be obtained (W/O or O/W). The emulsions may also contain stabilizers of other types, for instance fillers, gelling polymers or thickeners.

As emulsifying surfactants that may be used for the preparation of the W/O emulsions, exemplary are sorbitan, glycerol or sugar alkyl esters or ethers; silicone surfactants, for instance dimethicone copolyols, such as the mixture of cyclomethicone and of dimethicone copolyol, marketed under the trademark "DC 5225 C" by Dow Corning, and alkyldimethicone copolyols such as laurylmethicone copolyol marketed under the trademark "Dow Corning 5200 Formulation Aid" by Dow Corning; cetyidimethicone copolyol, such as the product marketed under the trademark Abil EM 90R by Goldschmidt, and the mixture of cetyldimethicone copolyol, of polyglyceryl isostearate (4 mol) and of hexyl laurate, marketed under the trademark Abil WE 09 by Goldschmidt. One or more co-emulsifiers may also be added thereto, which may be selected advantageously from the group comprising polyol alkyl esters.

Polyol alkyl esters that are especially exemplary include polyethylene glycol esters, for instance PEG-30 dipolyhydroxystearate, such as the product marketed under the trademark Arlacel P135 by ICI.

Glycerol and/or sorbitan esters that are especially exemplary include, for example, polyglyceryl isostearate, such as the product marketed under the trademark Isolan GI 34 by Goldschmidt, sorbitan isostearate, such as the product marketed under the trademark Arlacel 987 by ICI, sorbitan glyceryl isostearate, such as the product marketed under the trademark Arlacel 986 by ICI, and mixtures thereof.

For the O/W emulsions, examples of emulsifiers that are representative include non-ionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters, for instance the mixture PEG-100 stearate/glyceryl stearate marketed, for example, by ICI under the trademark Arlacel 165; oxyalkylenated (oxyethylenated and/or oxypropylenated) fatty alkyl ethers; sugar esters, for instance sucrose stearate; fatty alkyl ethers of sugars, especially polyalkylglucosides (APG) such as decylglucoside and laurylglucoside marketed, for example, by Henkel under the respective names Plantaren 2000 and Plantaren 1200, cetostearyl glucoside optionally as a mixture with cetostearyl alcohol, marketed, for example, under the trademark Montanov 68 by SEPPIC, under the trademark Tegocare CG90 by Goldschmidt and under the trademark Emulgade KE3302 by Henkel, and also arachidyl glucoside, for example in the form of a mixture of arachidyl alcohol, behenyl alcohol and arachidyl glucoside, marketed under the trademark Montanov 202 by SEPPIC. According to one particular embodiment of the invention, the mixture of the alkylpolyglucoside as defined above with the corresponding fatty alcohol may be in the form of a self-emulsifying composition as described, for example, in WO-A-92/06778.

Among the other emulsion stabilizers that will be used more particularly are isophthalic acid or sulfoisophthalic acid polymers, and, in particular, phthalate/sulfoisophthalate/glycol copolymers, for example the diethylene glycol/phthalate/isophthalate/1,4-cyclohexanedimethanol copolymer (INCI name: Polyester-5) marketed under the trademark "Eastman AQ Polymer" (AQ35S, AQ38S, AQ55S and AQ48 Ultra) by Eastman Chemical.

When it is an emulsion, the aqueous phase of this emulsion may comprise a non-ionic vesicular dispersion prepared according to known processes (Bangham, Standish and Watkins, *J. Mol. Biol.*, 13, 238 (1965), FR-2,315,991 and FR-2,416,008).

The compositions according to the invention find application in a large number of treatments, whether regime or regimen, especially cosmetic treatments, of the skin, the lips and the hair, including the scalp, especially for protecting and/or caring for the skin, the lips and/or the hair, and/or for making up the skin and/or the lips.

The present invention also features formulating the subject compositions as defined above for the manufacture of cosmetic products for treating the skin, the lips, the nails, the hair, the eyelashes, the eyebrows and/or the scalp, especially care products, anti-sun/sunscreen products and makeup products.

The cosmetic compositions according to the invention may be used, for example, as makeup products.

According to one preferred embodiment, the viscosity of the compositions, measured using a Rheomat 180 viscometer at 25° C. and at a spin speed of 200 rpm after spinning for 30 seconds, is less than or equal to 0.5 Pa·s.

According to one particularly preferred embodiment, the compositions according to the invention are in vaporizable fluid form applied to the skin or the hair in the form of fine particles by means of pressurization devices.

According to the invention, the term "vaporizable composition" is generally intended to mean any composition that can, under pressure in a suitable device, produce fine particles.

The present invention also features a pressurization device comprising (A) at least one reservoir containing at least one vaporizable fluid composition comprising, in a cosmetically acceptable aqueous support:

(a) at least one photoprotective system capable of screening out UV radiation as defined above; and (b) at least one ester-terminated poly(ester amide) (ET-PEA) polymer as defined above;

and (B) means for placing the said composition under pressure.

The devices in accordance with the invention are well known to those skilled in this art and comprise non-aerosol pumps or "atomizers", one- or two-compartment aerosol containers comprising a propellant, and also aerosol pumps using compressed air as propellant. These pumps are described in U.S. Pat. Nos. 4,077,441 and 4,850,517.

The compositions packaged in one-compartment aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

The two-compartment aerosols are provided with a pocket in which the composition in accordance with the invention is present. The propellant is located in the can and to the exterior of the pocket. It remains inside the device during use and exerts pressure on the pocket. This propellant may be a liquefied gas such as the propellants used in one-compartment aerosols, but also a compressed gas, for instance air or nitrogen.

In order to further illustrate the present invention and the advantages thereof, the following specific examples are given, it being understood that same are intended only as illustrative and in nowise limitative. In said examples to follow, all parts and percentages are given by weight, unless otherwise indicated.

The following anti-sun/sunscreen formulations were prepared; the amounts are given as weight percentages.

EXAMPLES 1 AND 2

Vaporizable fluid anti-sun/sunscreen formulations containing the following ingredients were prepared.

| Ingredients | Ex. 1 | Ex. 2 |
|---|---|---|
| Ethylhexyl salicylate (Neo Heliopan OS) | 5.0 | 5.0 |
| Butylmethoxydibenzoylmethane (Parsol 1789 - DSM) | 4.0 | 4.0 |
| Octocrylene (Uvinul N539 - BASF) | 3.5 | 3.5 |
| bis-Ethylhexyloxyphenol methoxyphenyl triazine (Tinosorb S - Ciba) | 3.0 | 3.0 |
| Ethylhexyl triazone (Uvinul T150 - BASF) | 2.5 | 2.5 |
| Terephthalylidenecamphorsulfonic acid | 1.0 | 3.0 |

-continued

| Ingredients | Ex. 1 | Ex. 2 |
|---|---|---|
| (Mexoryl SX - Chimex) | | |
| Drometrizole trisiloxane (Mexoryl X - Chimex) | 1.5 | 1.5 |
| Titanium dioxide (Microtitanium Dioxide MT 100 AQ - Tayca) | 3.5 | 3.5 |
| Denatured ethyl alcohol | 4.3 | 4.3 |
| $C_{12}$-$C_{15}$ alkyl benzoate | 12.5 | 12.5 |
| Glycerol | 6 | 6 |
| Tocopheryl (and) soybean glycin | 0.2 | 0.2 |
| Pentasodium salt of ethylenediaminetetra-methylenephosphonic acid at 33% in water (Dequest 2046 - Solutia) | 0.3 | 0.3 |
| Propylene glycol | 6.0 | 6.0 |
| Ethylhexyl glycerin (Sensitiva SC 50 - Schulke & Mayr) | 0.5 | 0.5 |
| Polyester-5 (Eastman AQ 38S - Eastman Chemical) | 2.0 | 2.0 |
| Bis-Stearyl ethylenediamine/neopentyl glycol/stearyl hydrogenated dimer dilinoleate copolymer (Sylvaclear C75 V - Arizona Chemical) | 1.5 | 1.5 |
| Polyacrylate-3 as a 25% emulsion in water (Viscophobe DB 1000 - Amerchol) | 0.7 | 0.7 |
| Triethanolamine | 0.7 | 0.66 |
| Demineralized water | qs 100 | qs 100 |

The composition does not fluff when applied to the skin.

A comparative anti-sun/sunscreen formulation 2 of the same composition as formulation 1, but not containing any ETPEA polymer, was then prepared.

The viscosities of compositions 1 and 2, measured using a Rheomat 180 viscometer at 25° C. at a spin speed of 200 rpm after 30 seconds, are, respectively, 0.32 Pa·s and 0.27 Pa·s.

For each of the compositions 1 and 2, the sun protection factor (SPF) associated therewith was then determined. This was determined by using the in vitro method described by B. L. Diffey et al., in *J. Soc. Cosmet. Chem.*, 40, 127-133 (1989); this method consists in determining the monochromatic protection factors over a wavelength range from 290 to 400 nm and in calculating therefrom the sun protection factor according to a given mathematical equation. The measurement was performed with a 1 nm interval on a UV-1000S machine from Labsphere, 0.6 mg/cm$^2$ of product being spread onto a frosted PMMA plate.

The results (mean value corresponding to 5 plates per product, 8 points per plate) are collated in Table (I) below:

TABLE (I)

| | Composition | |
|---|---|---|
| | 1 (invention) with ETPEA polymer | 2 (outside the invention) without ETPEA polymer |
| Mean SPF (standard deviation) | 101.9 (16.2) | 64.4 (9.7) |

EXAMPLES 3 AND 4

Outside the Invention

The anti-sun/sunscreen composition 3 of Example 2 of WO 2006/001940 containing the polymer bis-stearyl ethylenediamine/neopentyl glycol/stearyl hydrogenated dimer dilinoleate copolymer below and a corresponding composition 4 not containing the said polymer were prepared.

| Ingredients | Ex. 3 | Ex. 4 |
|---|---|---|
| Phase A | | |
| Deionized water | 48.05 | 49.55 |
| PEMULEN TR1 | 0.38 | 0.38 |
| Propyleneglycol | 5.0 | 5.0 |
| Disodium EDTA | 0.01 | 0.01 |
| Preservative | 1.0 | 1.0 |
| Phase B | | |
| Octinoxate | 7.5 | 7.5 |
| Oxybenzone | 6.0 | 6.0 |
| Vitamin E, DL alpha tocopherol | 0.01 | 0.01 |
| Oleth-3 | 0.2 | 0.2 |
| Octylsalicylate | 5.0 | 5.0 |
| Homenthyl salicylate | 13.0 | 13.0 |
| Bis-Stearyl Ethylenediamine/Neopentyl Glycol/Stearyl Hydrogenated Dimer Dilinoleate Copolymer (SYLVACLEAR C75 V-ARIZONA CHEMICAL) | 1.5 | — |
| Octocrylene | 2.0 | 2.0 |
| Phase C | | |
| Deionized water | 10 | 10 |
| Triethanolamine | 0.35 | 0.35 |
| Phase D | | |
| Perfume | qs | qs |

The viscosities of compositions 3 and 4, measured using a Rheomat 180 viscometer at 25° C. at a spin speed of 200 rpm after 30 seconds, are, respectively, 2.0 Pa·s and 1.9 Pa·s.

For each of the compositions 3 and 4, the sun protection factor (SPF) associated therewith was then determined. This was determined by using the in vitro method described by B. L. Diffey et al., in *J. Soc. Cosmet. Chem.*, 40, 127-133 (1989); this method consists in determining the monochromatic protection factors over a wavelength range from 290 to 400 nm and in calculating therefrom the sun protection factor according to a given mathematical equation. The measurement was performed with a 1 nm interval on a UV-1000S machine from Labsphere, 0.6 mg/cm$^2$ of product being spread onto a frosted PMMA plate.

The results (mean value corresponding to 5 plates per product, 8 points per plate) are collated in Table (I) below:

TABLE (II)

| | Composition | |
|---|---|---|
| | 3 (invention) with ETPEA polymer | 4 (outside the invention) without ETPEA polymer |
| Mean SPF (standard deviation) | 34.4 (5.7) | 36.4 (4.5) |
| Viscosity | 2.0 Pa·s | 1.9 Pa·s |

In composition 3, which is not fluid within the meaning of the invention, corresponding to Example 2 of WO 2006/001940, it is observed that the ETPEA polymer does not allow the SPF to be increased.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically fluid composition useful for photoprotecting the skin and/or the hair against the damaging effects of ultraviolet radiation, comprising:
    (a) at least one photoprotective system capable of screening out UV radiation comprising:
        (i) one or more hydrophilic lipophilic or insoluble organic screening agents selected from the group consisting of anthranilates; cinnamates; dibenzoylmethanes; salicylates; benzylidenecamphors; triazines; benzophenones; β-diphenylacrylates; benzotriazoles; benzalmalonates; benzimidazoles; imidazolines; bis-benzazolyls; p-aminobenzoates; methylenebis(hydroxyphenylbenzotriazoles);
        screening polymers and screening silicones; α-alkylstyrene-based dimers; 4,4-diarylbutadienes, and mixtures thereof; and/or
        (ii) one or more mineral (nano) pigments selected from the group consisting of coated metal oxides and uncoated metal oxides;
    (b) at least one ester-terminated poly(ester amide) (ETPEA) polymer which comprises bis-stearyl ethylenediamine/neopentyl glycol/stearyl hydrogenated dimer dilinoleate copolymer, formulated into
    (c) a topically applicable, cosmetically acceptable aqueous composition,
    said composition having a viscosity, measured using a Rheomat 180 viscometer at 25° C. at a spin speed of 200 rpm after spinning for 30 seconds, of less than or equal to 0.5 Pa·s,
    wherein said composition has an increased SPF relative to the composition without the at least one ester-terminated poly(ester amide) (ETPEA) polymer.

2. The photoprotective composition as defined by claim 1, in which the ester-terminated poly(ester amide) polymer is present therein in a maximum amount of 10% by weight relative to the total weight of the composition.

3. The photoprotective composition as defined by claim 2, in which the ester-terminated poly(ester amide) polymer is present therein in an amount ranging from 1% to 3% relative to the total weight of the composition.

4. The photoprotective composition as defined by claim 1, comprising at least one organic screening agent selected from the group consisting of:
Ethylhexyl methoxycinnamate
Homosalate,
Ethylhexyl salicylate,
Butylmethoxydibenzoylmethane,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Ethylhexyl Triazone,
Bis-Ethylhexyloxyphenol Methoxyphenyl Triazine,
Diethylhexyl Butamido Triazone,
2,4,6-tris(Dineopentyl 4'-aminobenzalmalonate)-s-triazine,
2,4,6-tris(Diisobutyl 4'-aminobenzalmalonate)-s-triazine,
Methylenebis(benzotriazolyl)tetramethylbutylphenol,
Drometrizole trisiloxane, Polysilicone-15,
Dineopentyl 4'-methoxybenzalmalonate,
1,1-Dicarboxy(2,2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine,
and mixtures thereof.

5. The photoprotective composition as defined by claim 1, wherein said metal oxide is selected from the group consisting of titanium oxide, iron oxide, zinc oxide, zirconium oxide and cerium oxide.

6. The photoprotective composition as defined by claim 1, in which the photoprotective system is present in a content ranging from 0.1% to 40% by weight relative to the total weight of the composition.

7. The photoprotective composition as defined by claim 1, further comprising at least one self-tanning agent.

8. The photoprotective composition as defined by claim 1, further comprising at least one cosmetic adjuvant selected from the group consisting of fatty substances, organic solvents, ionic or non-ionic, hydrophilic or lipophilic thickeners, softeners, humectants, opacifiers, stabilizers, emollients, silicones, anti-foams, fragrances, preservatives, anionic, cationic, non-ionic, zwitterionic or amphoteric surfactants, active agents, fillers, polymers, propellants, acidifying or basifying agents, any other ingredient usually employed in cosmetics and/or dermatology, and mixtures thereof.

9. The photoprotective composition as defined by claim 1, formulated as a simple or complex emulsion; a cream gel; an aqueous gel; a lotion, or as an aerosol in the form of a mousse or spray, or packaged as an atomizer.

10. The photoprotective composition as defined by claim 1, formulated as an oil-in-water or water-in-oil emulsion.

11. The photoprotective composition as defined by claim 10, comprising at least one isophthalic acid or sulfoisophthalic acid polymer.

12. The photoprotective composition as defined by claim 11, in which the said isophthalic acid or sulfoisophthalic acid polymer comprises Polyester-5.

13. The photoprotective composition as defined by claim 1, in vaporizable form.

14. A regime or regimen for photoprotecting the skin and/or the hair against the damaging effects of UV radiation, comprising topically applying thereof a thus effective amount of the photoprotective composition as defined by claim 1.

15. The photoprotective composition as defined by claim 1, wherein the at least one photoprotective system capable of screening out UV radiation comprises butylmethoxydibenzoylmethane.

16. The photoprotective composition as defined by claim 5, wherein said metal oxide a nonpayment.

* * * * *